United States Patent
Kappler et al.

(10) Patent No.: US 9,192,341 B2
(45) Date of Patent: Nov. 24, 2015

(54) COMPUTED TOMOGRAPHY DEVICE AND METHOD FOR OPERATING A COMPUTED TOMOGRAPHY DEVICE

(71) Applicant: SIEMENS AKTIENGESELLSCHAFT, Munich (DE)

(72) Inventors: Steffen Kappler, Effeltrich (DE); Martin Petersilka, Adelsdorf (DE); Karl Stierstorfer, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 345 days.

(21) Appl. No.: 13/764,865

(22) Filed: Feb. 12, 2013

(65) Prior Publication Data
US 2013/0208854 A1    Aug. 15, 2013

(30) Foreign Application Priority Data
Feb. 13, 2012  (DE) .......................... 10 2012 202 107

(51) Int. Cl.
  *A61B 6/03*  (2006.01)
  *A61B 6/00*  (2006.01)
  *G01T 1/29*  (2006.01)

(52) U.S. Cl.
  CPC ............... *A61B 6/032* (2013.01); *A61B 6/4233* (2013.01); *A61B 6/542* (2013.01); *G01T 1/2985* (2013.01)

(58) Field of Classification Search
  CPC ........ A61B 6/00; A61B 6/032; A61B 6/4085; A61B 6/5205; A61B 6/027; A61B 6/542; A61B 6/2985; A61B 6/4233; G01T 1/2985; G01N 2223/419; G01N 23/046
  USPC ............ 378/4, 19, 21, 91, 115, 116; 250/363.04, 370.09; 400/621
  See application file for complete search history.

(56) References Cited

U.S. PATENT DOCUMENTS

| | | | | |
|---|---|---|---|---|
| 4,759,047 A | * | 7/1988 | Donges et al. | 378/57 |
| 5,023,895 A | * | 6/1991 | McCroskey et al. | 378/4 |
| 5,448,609 A | | 9/1995 | Couch et al. | |
| 5,764,721 A | * | 6/1998 | Light et al. | 378/4 |
| 2007/0102642 A1 | | 5/2007 | Spahn | |
| 2007/0195926 A1 | * | 8/2007 | Munker et al. | 378/19 |

FOREIGN PATENT DOCUMENTS

| DE | 19502574 A1 | 8/1996 |
|---|---|---|
| DE | 19502574 C2 | 9/1999 |

(Continued)

OTHER PUBLICATIONS

German Priority Document German Application 10 2012 202 107.8, Feb. 13, 2012.

*Primary Examiner* — Irakli Kiknadze
*Assistant Examiner* — Julio M Duarte-Carvajalino
(74) *Attorney, Agent, or Firm* — Harness, Dickey & Pierce, P.L.C.

(57) ABSTRACT

A method is disclosed for operating a computed tomography device including an x-ray source embodied to emit a fan-type beam bundle and a detector arrangement interacting therewith and including a plurality of detector elements. An embodiment of the method provides that an integration time provided to read out a detector element is dependent on the position of the detector element within the detector arrangement, wherein with a detector element which detects x-rays which penetrate the isocenter lying between the x-ray source and the detector arrangement, a longer integration time is provided, than with a detector element which detects x-rays which penetrate an examination volume which is further away from the isocenter.

9 Claims, 1 Drawing Sheet

(56) References Cited

FOREIGN PATENT DOCUMENTS

| DE | 10-2005053993 | A1 | 5/2007 |
| DE | 102005053993 | A1 | 5/2007 |
| EP | 0647347 | B1 | 9/1998 |
| EP | 0647347 | B1 | 9/1998 |
| WO | WO 94/00850 | | 1/1994 |

* cited by examiner

COMPUTED TOMOGRAPHY DEVICE AND METHOD FOR OPERATING A COMPUTED TOMOGRAPHY DEVICE

PRIORITY STATEMENT

The present application hereby claims priority under 35 U.S.C. §119 to German patent application number DE 10 2012 202 107.8 filed Feb. 13, 2012, the entire contents of which are hereby incorporated herein by reference.

FIELD

At least one embodiment of the invention generally relates to a computed tomography device which can be used in particular as a medical diagnosis device and/or to a method for operating a computed tomography device.

BACKGROUND

DE 10 2005 053 993 A1 discloses a diagnosis apparatus and a diagnosis method for combined and/or combinable radiographic and nuclear-medical examinations. The diagnosis apparatus includes an x-ray source, which generates x-rays for examination of the human body. Provision is furthermore made to position radioactive substances, which emit gamma radiation, in a tissue to be examined. The energies of the x-ray quanta and the energies of the gamma quanta are to lie in a similar range.

A detector system, which includes a plurality of pixels arranged in rows and columns, is embodied to simultaneously measure the x-ray and gamma quanta. The integration time of the individual pixels can be selectively or jointly adjusted by means of control electronics. An exposure time can thus be predetermined, during which the intensity of incident x-ray and/or gamma radiation is integrated pixel by pixel over time.

DE 195 02 574 C2 discloses a computed tomography device having an x-ray emitter to emit a conical x-ray bundle and a two-dimensional detector. The detector consists here of several parallel detector rows, which are each embodied from a series of detector elements.

EP 0 647 347 B1 discloses a further computed tomography device, which includes a detector arrangement having a plurality of individual detector elements, for instance 4800. The complexity of the processing electronics is to be reduced by two or more detector elements being connected to form a pseudo detector.

SUMMARY

At least one embodiment of the invention is directed to a computed tomography device including a plurality of detector elements.

A method and a computed tomography device are disclosed. Embodiments and advantages explained below in conjunction with the method naturally also apply to the computed tomography devices and vice versa. A computer program product enables operation of a computed tomography device.

At least one embodiment of the invention assumes that a target conflict between the spatial resolution and the detector noise typically exists in a computed tomography device. A high number of read-out processes is needed per revolution of the x-ray emitter detector unit in order to achieve a high resolution. The high number of read out processes neverthe-less corresponds to a low integration time for the individual read-out processes, which tends to indicate a higher detection noise.

BRIEF DESCRIPTION OF THE DRAWINGS

Example embodiments of the invention are then explained in more detail with the aid of a drawing, in which.

Figure 1:
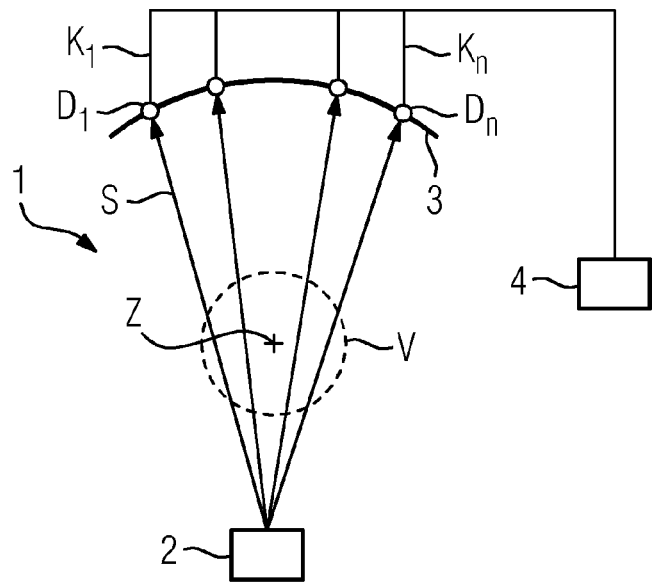
FIG. 1 shows a computed tomography device in a schematic representation.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention assumes that a target conflict between the spatial resolution and the detector noise typically exists in a computed tomography device. A high number of read-out processes is needed per revolution of the x-ray emitter detector unit in order to achieve a high resolution. The high number of read out processes nevertheless corresponds to a low integration time for the individual read-out processes, which tends to indicate a higher detection noise.

This target conflict is as a result efficiently approached according to at least one embodiment of the inventive method in that an integration time provided to read-out a detector element is dependent on the position of the detector element within the detector arrangement. At least one embodiment of the invention can be applied in a computed tomography device, which comprises an x-ray source embodied to emit a fan-type beam bundle and a detector arrangement interacting herewith and comprising a plurality of detector elements.

The position-dependent integration time of the individual detector elements enables the read-out process to be adjusted to the conditions provided at the respective location, which relate to signal noise and spatial resolution.

With a detector element which detects x-rays which penetrate the isocenter of the computed tomography device disposed between the x-ray source and the detector arrangement, a longer integration time is provided than with a detector element which detects x-rays which penetrate through an examination object when further away from the isocenter. The isocenter is defined as the center of a fictitious image reconstruction circuit, within the periphery of which an object to be scanned and to be reconstructed lies in the examination volume. The integration time is therefore longer, the closer a detector element is to the center of the detector arrangement.

For instance, the maximum integration time provided with at least one detector element in the center of the detector arrangement is twice the minimum integration time provided with at least one detector element at the edges of the detector arrangement. In an example embodiment, the integration time of each detector element without a minimal integration time is a whole number multiple of the shortest integration time used in one of the detector elements within the detector arrangement. This use of exclusively whole number multiples of the lowest integration time allows for simple synchronization of the data read out. Other multiples of the integration time which are not whole numbers are in principle also possible however.

According to a particularly simple variant, precisely two different integration times are provided, namely the simple integration time at the two edges (observed in the peripheral direction) of the detector arrangement, and the double integration time in the center of the detector arrangement. Angular ranges of the detector arrangement referred to here as edges herewith extend in each instance across 20% to 30%, in particular across a quarter of the entire extension of the detector arrangement.

An even more precise adjustment of the read-out processes to the geometry of the entire arrangement comprising x-ray emitter, examination volume and detector is possible by the integration time varying in at least three stages irrespective of the position of a detector element within the detector arrangement. In a theoretical extreme case, an integration time which differs from the adjacent detector elements is provided for each detector element. The location dependent integration time could thus form an almost continuous curve contrary to the afore-cited, particularly simple two-stage variant.

While a plurality of detector elements is arranged in the peripheral direction of the detector arrangement according to each variant, either only a single detector element or likewise a plurality of detector elements can be arranged for this purpose in the orthogonal direction, in other words in the axial direction of the rotatable x-ray emitter-detector arrangement. In the latter case, in other words with two-dimensionally arranged detector elements, the same integration time is preferably assigned to the detector elements placed one behind the other in the cited axial direction. In all instances, a signal provided by a detector element or a signal provided by detector elements arranged one behind the other, in other words in a row, is typically read out by way of a channel in each instance and supplied to a computing unit. In simple terms, instead of the reading out of detector elements, reference is also made to the scanning of channels.

In all embodiments, lengthening the integration time in the central channels reduces the detector noise. Since these central channels amount to the entire image to be generated by means of the computed tomography device, the noise in the entire image reduces, particularly however in its center, since there only channels with a longer integration time contribute to the image.

An advantage of at least one embodiment of the invention lies in particular in the integration time of a channel, in other words of a detector element within a detector arrangement extending over a specific angular range, in the case of a computed tomography device of the third generation (see descriptions pertaining to the prior art in EP 0 647 347 B1), being dependent on the position of the channel, as a result of which a particularly favorable relationship is achieved between the spatial resolution and detector noises.

A computed tomography device only shown suggestively in FIG. 1 and identified with reference character 1 in the introduction in respect of its principle functionality, comprises an x-ray source 2 and a detector arrangement 3. The x-ray source 2 emits a fan-type beam bundle S, which is aligned with an examination volume V and strikes the detector arrangement 3 at least partially, said detector arrangement including a plurality, in the exemplary embodiment shown, thousands of detector elements D1 to Dn.

The signals provided by the individual detector D1 to Dn are supplied via channels K1 to Kn to a computing unit 4, which likewise forms a component of the computed tomography device 1. The computing unit 4 is herewith not necessarily arranged physically within the actual tomograph comprising the x-ray source 2 and the detector arrangement 3 and could for instance also be structured from several individual components, or realized decentrally within a data processing network.

The isocenter of the rotatable x-ray emitter detector unit comprising the x-ray source 2 and the detector arrangement 3, is identified with Z, an examination volume to be examined by means of the computed tomography device 1 and to be indicated by a dashed line is indicated with V. The detector elements D1 to Dn indicated by way of example in FIG. 1 are arranged adjacent to one another in the so-called channel direction, overall forming an arched design of the detector arrangement 3. Nevertheless, the detector elements D1 to Dn could also be arranged on a planar detector. In both instances, a number of detector elements D1 to Dn could be arranged at right angles to the drawing plane in FIG. 1 one behind other so that an array of detector elements D1 to Dn is formed overall.

In the example embodiment according to FIG. 1, it is assumed that in order to obtain image data by means of the computed tomography device 1, the x-ray source 2 and the detector arrangement 3 are moved, while the examination object is in an unchanged position. In application areas outside of medicine, it is however likewise possible to move the examination object, whereas the x-ray source 2 and the detector arrangement 3 are stationary.

Figure 2:
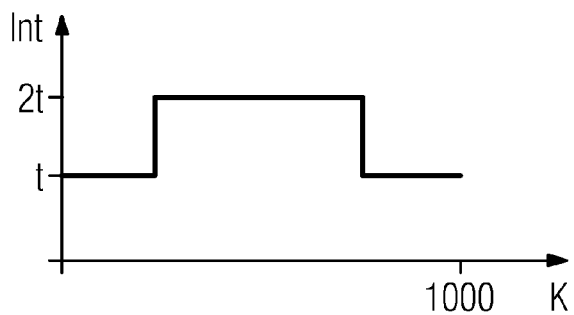
FIG. 2 shows by way of example in a diagram the dependency between the position of a channel of a detector of the computed tomography device according to FIG. 1 and an integration time provided to read out the channel, FIG. 3 a further example of the location-dependent determination of the integration time in a diagram according to FIG. 2.

A first example of the location-specific scanning of 1000 channels K1 to K1000 (n=1000) of the computed tomography device 1 is indicated in FIG. 2. A uniform, simple integration time t is assigned to the channels K1 to K250 (in FIG. 1 at the left edge of the detector arrangement 3) as integration time Int. The central channels K251 to K750 by contrast have twice the integration time 2t. The channels K751 to K1000 to the right in the arrangement according to FIG. 1 are in turn scanned with the simple integration time t according to the left channels K1 to K250. A rough but effective adjustment of the integration time Int to the position of the channels K1 to Kn and thus also to the detector elements D1 to Dn is provided overall.

Figure 3:
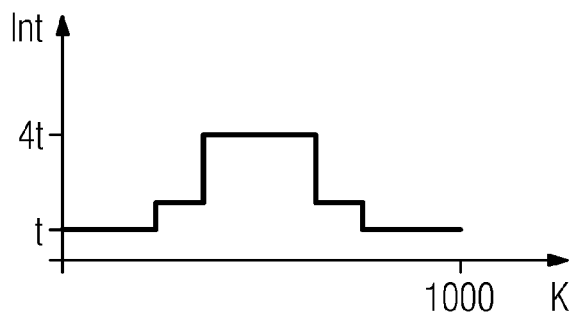

In the example embodiment according to FIG. 2, the adjustment of the integration time Int is refined by comparison with the example embodiment according to FIG. 1, wherein the variant according to FIG. 3 can also be realized by means of the computing unit 4 in the case of computed tomography according to FIG. 1.

As apparent in the diagram according to FIG. 3, provision is made for a three-stage, location-dependent variation of the integration time Int. The simple integration time t is applied to the outer channels K1 to K250 and K751 to K1000. The central channels K376 to K625 are operated with the fourfold integration time 4t. With the channels K251 to K375 and K626 to K750 lying between the outer and the central channels, the double integration time 2t is determined. With a further improvement of the variants according to FIGS. 2 and 3, significantly smaller stages of the integration time Int can still also be realized up to an approximately continuous change in the integration time In in the channel direction of the detector arrangement 3.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating a computed tomography device including an x-ray source and a detector arrangement, the x-ray source being configured to emit a fan-type beam bundle, the detector arrangement including a plurality of detector elements, and the detector arrangement being configured to interact with the x-ray source, wherein integration times to read out the plurality of detector elements are dependent on positions of the plurality of detector elements within the detector arrangement, the method comprising:

providing a longer integration time for at least a first detector element configured to detect x-rays which penetrate the isocenter, disposed between the x-ray source and the detector arrangement, than for at least a second detector element configured detect x-rays which penetrate an examination volume relatively further away from the isocenter, wherein the integration times vary in at least three stages as a function of the positions of the plurality of detector elements within the detector arrangement.

2. The method of claim 1, wherein the first detector element is at a center of the detector arrangement; and a maximum integration time for the first detector element, is twice a minimal integration time an edge of the detector arrangement.

3. The method of claim 2, wherein the integration time for each detector element with a non-minimal integration time is a whole number multiple of a shortest integration time applied at an edge of the detector arrangement.

4. The method of claim 1, wherein the integration time of each of the plurality of detector elements with a non-minimal integration time is a whole number multiple of a shortest integration time applied at an edge of the detector arrangement.

5. The method of claim 1, wherein a maximum integration time for at least one of the plurality of detector elements is at least four times a minimal integration time for another of the plurality of detector elements of the detector arrangement.

6. A non-transitory computer readable medium storing program codes configured to produce the method of claim 1 when executed on a computing unit.

7. A non-transitory computer readable medium including program segments for, when executed on a computer device, causing the computer device to implement the method of claim 1.

8. A computed tomography device comprising:

an x-ray source configured to emit a fan-type beam bundle; and a detector arrangement including a plurality of detector elements, the detector arrangement being configured to interact with the x-ray source, wherein integration times to read out the plurality of detector elements are dependent on positions of the plurality of detector elements within the detector arrangement, a relatively longer integration time is provided for at least a first detector element configured to detect x-rays which penetrate the isocenter, disposed between the x-ray source and the detector arrangement, than for at least a second detector element configured detect x-rays which penetrate an examination volume relatively further away from the isocenter, and the integration times vary in at least three stages as a function of the positions of the plurality of detector elements within the detector arrangement.

9. The computed tomography device of claim 8, wherein a maximum integration time for at least one of the plurality of detector elements is at least four times a minimal integration time for another of the plurality of detector elements of the detector arrangement.

* * * * *